United States Patent
Hamou

(10) Patent No.: US 8,267,933 B2
(45) Date of Patent: Sep. 18, 2012

(54) DEVICE FOR RESECTION AND/OR ABLATION OF ORGANIC TISSUE BY MEANS OF HIGH-FREQUENCY CURRENT AND RESECTOSCOPE

(76) Inventor: Jacques Hamou, Paris (FR)

(*) Notice: Subject to any disclaimer, the term of this patent is extended or adjusted under 35 U.S.C. 154(b) by 1129 days.

(21) Appl. No.: 11/842,592

(22) Filed: Aug. 21, 2007

(65) Prior Publication Data

US 2008/0045945 A1 Feb. 21, 2008

(30) Foreign Application Priority Data

Aug. 21, 2006 (DE) .......................... 10 2006 039 696

(51) Int. Cl.
*A61B 18/14* (2006.01)
(52) U.S. Cl. ................. 606/46; 606/41; 606/45
(58) Field of Classification Search .......... 600/104–105; 606/32–50
See application file for complete search history.

(56) References Cited

U.S. PATENT DOCUMENTS

| | | | | |
|---|---|---|---|---|
| 3,955,578 | A * | 5/1976 | Chamness et al. | 606/47 |
| 5,047,027 | A * | 9/1991 | Rydell | 606/48 |
| 5,100,423 | A * | 3/1992 | Fearnot | 606/159 |
| 5,207,686 | A * | 5/1993 | Dolgin | 606/113 |
| 5,488,958 | A | 2/1996 | Topel et al. | 128/754 |
| 5,906,615 | A * | 5/1999 | Thompson | 606/45 |
| 6,013,076 | A * | 1/2000 | Goble et al. | 606/41 |
| 6,050,993 | A * | 4/2000 | Tu et al. | 606/41 |
| 6,093,185 | A * | 7/2000 | Ellis et al. | 606/28 |
| 6,217,575 | B1 * | 4/2001 | DeVore et al. | 606/41 |
| 6,224,611 | B1 * | 5/2001 | Ouchi | 606/113 |
| 6,245,067 | B1 * | 6/2001 | Tu et al. | 606/41 |
| 6,246,913 | B1 | 6/2001 | Sharkey | 607/101 |
| 6,267,759 | B1 * | 7/2001 | Quick | 606/47 |
| 6,402,740 | B1 * | 6/2002 | Ellis et al. | 606/28 |
| 6,454,727 | B1 * | 9/2002 | Burbank et al. | 600/567 |
| 6,743,228 | B2 * | 6/2004 | Lee et al. | 606/47 |
| 6,960,206 | B2 * | 11/2005 | Keane | 606/41 |
| 6,997,926 | B2 * | 2/2006 | Gellman et al. | 606/46 |
| 7,270,663 | B2 * | 9/2007 | Nakao | 606/47 |
| 7,387,632 | B2 * | 6/2008 | Ouchi | 606/47 |
| 2002/0049439 | A1 | 4/2002 | Mulier et al. | 606/41 |
| 2002/0183589 | A1 * | 12/2002 | Brommersma et al. | 600/105 |

(Continued)

FOREIGN PATENT DOCUMENTS

DE 848233 9/1952

(Continued)

OTHER PUBLICATIONS

German Search Report, May 23, 2007, 4 pages.

(Continued)

*Primary Examiner* — Michael Peffley
*Assistant Examiner* — Ronald Hupczey, Jr.
(74) *Attorney, Agent, or Firm* — St. Onge Steward Johnston & Reens LLC

(57) ABSTRACT

A device for removing organic tissue by means of high-frequency current comprises a loop carrier having a longitudinal axis and a distal end, a loop arranged at the distal end of the loop carrier and being able to be acted upon by high-frequency voltage, the loop having a loop end portion, a connection element connecting the loop with the loop carrier and having a distal connection element portion, the loop end portion and the distal connection element portion forming a wedge-shaped cutter.

5 Claims, 4 Drawing Sheets

U.S. PATENT DOCUMENTS

| | | | |
|---|---|---|---|
| 2003/0130653 A1* | 7/2003 | Sixto et al. | 606/45 |
| 2004/0064139 A1* | 4/2004 | Yossepowitch | 606/46 |
| 2004/0138654 A1 | 7/2004 | Goble | |
| 2004/0199048 A1* | 10/2004 | Clayman et al. | 600/104 |
| 2006/0089639 A1 | 4/2006 | Quick | |
| 2008/0009855 A1* | 1/2008 | Hamou | 606/46 |

FOREIGN PATENT DOCUMENTS

| | | |
|---|---|---|
| DE | 299 11 756 | 11/1999 |
| DE | 10 2005 013 847 | 9/2006 |
| EP | 1658812 | 5/2006 |
| WO | 98/15230 | 4/1998 |
| WO | 2006/048199 | 5/2006 |

OTHER PUBLICATIONS

European Search Report, Dec. 14, 2007, 6 Pages.

* cited by examiner

DEVICE FOR RESECTION AND/OR ABLATION OF ORGANIC TISSUE BY MEANS OF HIGH-FREQUENCY CURRENT AND RESECTOSCOPE

CROSS-REFERENCE TO RELATED APPLICATION

The present application claims priority of German patent application No. 10 2006 039 696.0 filed on Aug. 21, 2006.

BACKGROUND OF THE INVENTION

The invention generally relates to devices for removing, i.e. for resecting and/or ablating organic tissue by means of high-frequency current.

The invention further relates to a resectoscope for removing organic tissue by means of high-frequency current, comprising a shaft in which a device of the aforementioned type is arranged.

Such a device or resectoscope is used in high-frequency surgery for resection and ablation of organic tissue. The device can be used in particular in hysteroscopy or in urology, in order to remove fibromas, polyps and endometrial tissue, or prostatic adenomas.

A device of the type mentioned above is known from US 2004/0064139 A1 which comprises a loop carrier, an electrically conductive loop that can be acted upon by high-frequency current, and a connection element in the form of two rectilinear strands between the loop carrier and the loop. The loop extends either in a plane transverse to a longitudinal axis of the loop carrier or in a plane that contains the longitudinal axis of the loop carrier.

In order to remove organic tissue by means of the device received in the resectoscope, said device is moved by the physician along the longitudinal direction of the loop carrier. The loop that can be acted upon by high-frequency voltage thus separates the tissue to be removed in a pulling cut. At the same time, the surface of the cut is obliterated by means of the loop, in order to stanch any bleeding. The detached pieces of tissue have to be removed from the operating site in a further step.

All the embodiments of the arrangement of loop carrier, connection element and loop that are described in the aforementioned document US 2004/0064139 A1 have the disadvantage that they are only suitable for cutting tissue by means of a pulling cut, in which the loop is thus moved in the longitudinal direction of the loop carrier.

A further device of the type mentioned at the outset is known from WO 2006/048199 A1 and comprises a loop carrier in the form of a hollow tube, a loop arranged at the distal end of the loop carrier, and a connection element designed as double helix between the loop and the loop carrier. The loop has a semicircular shape and is inclined slightly towards a longitudinal axis of the loop carrier and can be acted upon by high-frequency voltage. This device cuts tissue by means of the loop and the double helix being moved in rotation about the longitudinal axis of the hollow tube. The co-rotating double helix is also intended to serve for transporting detached organic tissue in the proximal direction, and the tissue can additionally be suctioned in the proximal direction when introduced into the tube.

Depending on the topology of the tissue that is to be cut, the semicircular loop lies more or less in a line on the tissue at the start of the cut, it also being possible for individual sections of the loop to touch the tissue while others do not. This is the case when the tissue to be cut has convex and concave areas. In other words, there is no defined point on the loop at which the cut begins. The fact that the loop bears in a line at least in some areas on the tissue to be cut means that the cutting action of the known device is also not optimal. The same also applies to the device known from US 2004/0064139 A1, in which the loop, because of its symmetry, does not permit a defined start to the cut.

SUMMARY OF THE INVENTION

It is therefore an object of the present invention to create a device of the type mentioned at the outset that permits targeted and more effective removal of tissue.

According to an aspect of the invention, a device for removing organic tissue by means of high-frequency current is provided, comprising a loop carrier having a longitudinal axis and a distal end, a loop arranged at the distal end of the loop carrier and being able to be acted upon by high-frequency voltage, the loop having a loop end portion, a connection element connecting the loop with the loop carrier and having a distal connection element portion, the loop end portion and the distal connection element portion forming a wedge-shaped cutter.

The device according to the invention thus has a wedge-shaped cutter at its distal end. Here, "wedge-shaped" means that the distal connection element portion and the loop end portion converge at an acute angle, i.e. an angle of less than 90°. This connection is preferably made in one piece. The wedge-shaped cutter is suitable in particular for an embodiment of the device in which cutting is achieved by moving the loop in rotation. The wedge-shaped cutter forms a defined point of contact of the active cutting area of the loop on the tissue. By means of the wedge-shaped configuration of the cutter, the latter can penetrate effectively into the tissue to be cut and in so doing can at the same time detach or lift said tissue from the rest of the tissue. The device according to the invention advantageously permits resection and coagulation of tissue to the front of the loop and also of tissue located to the sides of the connection element and of the loop. The tissue located to the front is removed by the loop end portion and by the remaining area of the loop, while the tissue located to the sides can be removed at least by the distal connection element portion.

In a preferred embodiment, the loop extends in a plane transverse to a longitudinal axis of the loop carrier.

This measure has the advantage that, if the loop can be moved in rotation via the loop carrier, the loop, which is usually made from a thin wire, cuts through the tissue like a sickle in the longitudinal extent of the wire. In this way, the loop does not meet increased mechanical resistance during cutting and is at less risk of bending or even breaking.

In another preferred embodiment, the loop carrier can rotate about its longitudinal axis, and an end area of the wedge-shaped cutter points in the direction of rotation of the loop carrier.

In this embodiment, the wedge-shaped cutter thus forms the leading end of the loop when the loop carrier is moved in rotation about its longitudinal axis. The wedge-shaped cutter can thus penetrate effectively into the tissue in order to detach the latter. The wedge-shaped cutter cuts the tissue off effectively in cooperation with the remaining trailing portion of the loop.

In another preferred embodiment, the wedge-shaped cutter points slightly in the distal direction.

This measure has the advantage that the wedge-shaped cutter, because of the slight inclination in the distal direction, engages like a screw into the tissue, as a result of which no pressure, or only inappreciable pressure, has to be exerted in the direction of advance during cutting.

In another preferred embodiment, the connection element is designed in a helical line shape.

This measure has the advantage that the device has a compact structure at the distal end, and that the stability of the device is increased. Moreover, tissue located to the sides can also be continuously removed by the area of the windings bearing on the tissue, in the manner of a corkscrew-like sickle. This is particularly advantageous compared to a rectilinear design of the connection element, since the surgical procedure can be performed more quickly. Until the detached tissue has been completely detached, the screw-like design has the effect that the tissue is conveyed in the proximal direction by means of a relative movement to the connection element.

In another preferred embodiment, the connection element has a first strand and a second strand, a distal end area of the first strand forming the wedge-shaped cutter together with the loop end portion, and a distal end area of the second strand being connected to the end of the loop opposite the loop end portion.

This measure has the advantage that the stability of the connection element against external forces during the cutting procedure is increased, since the loop is connected to the connection element not only in the area of the wedge-shaped cutter, but also at a second end, such that it is resistant in particular to torsional forces that may occur during rotary cutting with the loop.

In another preferred embodiment, the first strand and second strand of the connection element are wound in the shape of helical lines running in opposite directions.

This measure contributes to still better twist resistance of the loop relative to the loop carrier. In this way, solid tissue can also be reliably removed.

In another preferred embodiment, the loop has an approximately semicircular shape. This measure known per se, in combination with the design of a wedge-shaped cutter on one loop end portion, has the advantage of a particularly efficient cutting action of the loop, because the trailing cutting area of the loop is sufficiently great.

In another embodiment, the loop has a cutting edge on the inside and/or outside.

This measure has the advantage that the loop has a tissue-removing action not only in the area of the wedge-shaped cutter, but also in its remaining area, as a result of which the cutting efficiency of the device according to the invention is further improved.

In another preferred embodiment, the connection element has a cutting edge on the inside and/or outside at least in the area of the distal connection element portion.

This measure has the advantage that tissue located to the sides can also be effectively removed. During the rotation movement of the loop carrier, the cutting edge arranged preferably on the outside and inside of the connection element portion penetrates into the tissue to be removed and cuts through the latter in a sharp cut.

In another preferred embodiment, the loop carrier is designed as a hollow tube.

This measure has the advantage that tissue removed by means of the loop and, if appropriate, by means of the connection element can be guided through the hollow tube out of the body, for example by applying a suction current to the proximal end of the hollow tube. In this way, the detached tissue is permanently conveyed out of the body, without the detached tissue having to be removed by means of an additional instrument.

According to another aspect of the present invention, a resectoscope for removing organic tissue by means of high-frequency current is provided, which comprises a device according to one or more of the afore-mentioned embodiments.

Further advantages and features will become evident from the following description and from the attached drawing.

It will be appreciated that the aforementioned features, and the features still to be explained below, can be used not only in the cited combinations, but also in other combinations or singly, without departing from the scope of the present invention.

BRIEF DESCRIPTION OF THE DRAWINGS

The invention is described and explained in more detail below on the basis of selected illustrative embodiments and with reference to the attached drawing, in which.

DETAILED DESCRIPTION OF PREFERRED EXEMPLARY EMBODIMENTS

Figure 1:
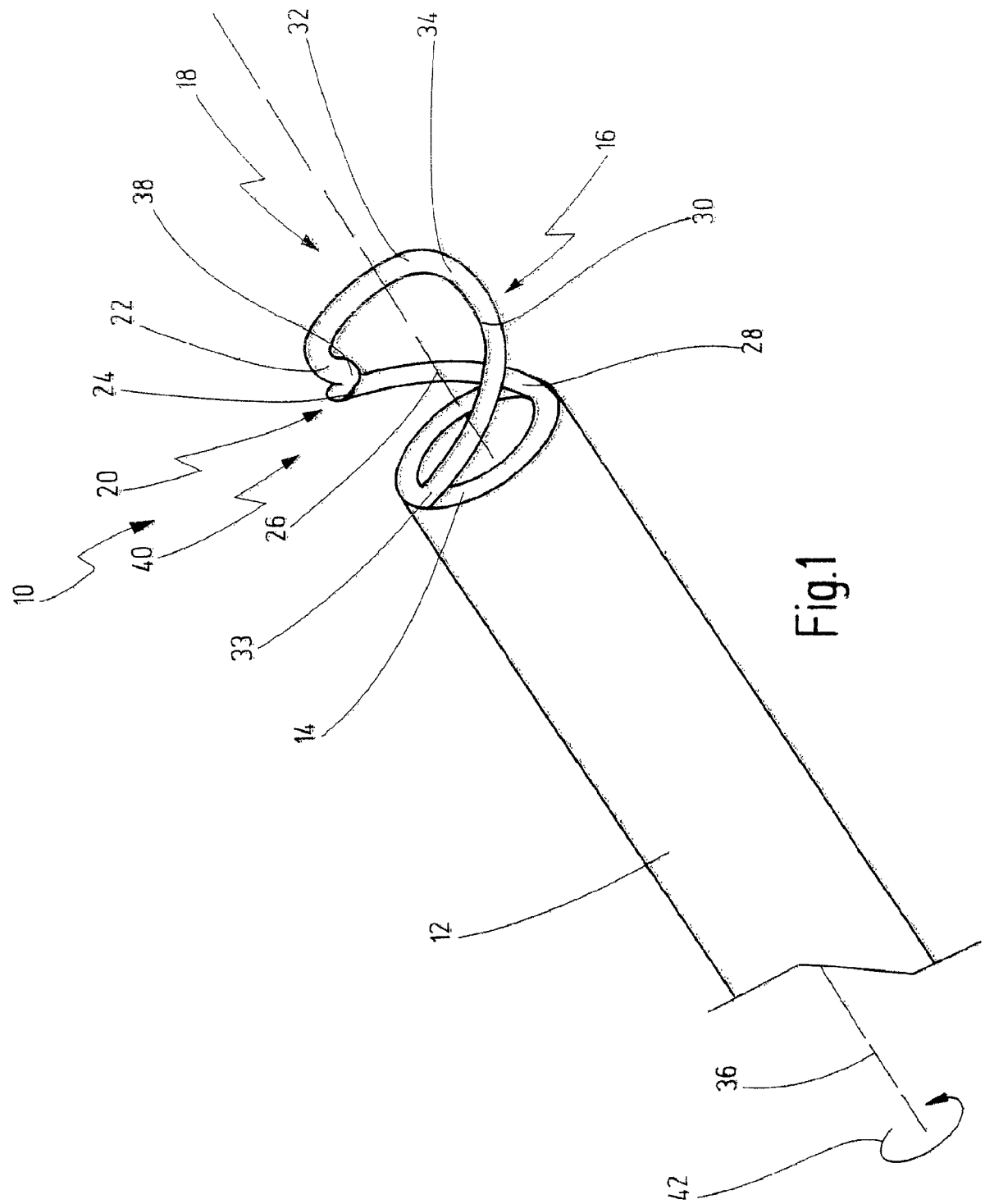
FIG. 1 shows a perspective view of a device for resection and/or ablation of organic tissue by means of high-frequency current.

A device for resection and/or ablation of organic tissue by means of high-frequency current is indicated in FIG. 1 by general reference number 10.

The device 10 can be used in hysteroscopy or urology, for example, in order to remove fibromas, polyps and endometrial tissue, or prostatic adenomas.

The device 10 has a loop carrier 12 at whose distal end 14 there is a connection element 16 and also a loop 18 that can be acted upon by high-frequency voltage.

The loop carrier 12 is designed as a cylindrical hollow tube, and the connection element 16 is connected to an annular front face of the distal end 14 of the hollow tube.

A distal connection element portion 20 of the connection element 16 is connected in a wedge shape to a loop end portion 22 of the loop 18, i.e. the connection element portion 20 and the loop end portion converge at an acute angle of less than 90°.

At least the distal connection element portion 20 is, like the loop 18, designed to convey current and is not insulated on the outside.

In the illustrative embodiment shown, the connection element portion 20 represents a distal end area 24 of a first strand 26 of the connection element 16, the first strand 26 being connected at a proximal end 28 to the distal end 14 of the loop carrier 12. The connection element 16 also comprises a second strand 30, which is arranged between the distal end 14 of the loop carrier 12 and an end 32 of the loop 18. For this purpose, a proximal end 33 of the second strand 30 is connected to the distal end 14 of the loop carrier 12 at a position offset by approximately 180° relative to the connection site of the first strand 26 to the distal end 14 of the loop carrier 12, and a distal end area 34 of the second strand 30 is connected to the loop end 32.

The loop end portion 22 and the distal end area 24 of the first strand 26 are connected to one another at an acute angle, i.e. at a small angle of less than 90°.

The loop 18 and the strands 26, 30 are formed as wires.

The connection element 16 is designed in a helical line shape, with both strands 26, being wound in the shape of helical lines running in opposite directions, i.e. they each have counterdirectional windings that are offset by a half lead, seen in a longitudinal direction 36 of the loop carrier 12. Each strand 26, 30 has a half winding. The two strands 26, 30 of the connection element 16 can also have several windings.

The loop 18 extends in a plane transverse to the longitudinal axis 36 of the loop carrier 12. In the illustrative embodiment shown, the loop 18 extends in the plane approximately perpendicular to the longitudinal axis 36 of the loop carrier 12. A corner 38 in the area of the connection of the connection element portion 20 to the loop end portion 22 forms a wedge-shaped cutter 40 lying in the plane of the loop 18. The wedge-shaped cutter 40 can also point slightly in the distal direction, in which case the plane in which the loop extends can also deviate from a perpendicular arrangement relative to the longitudinal axis 36 of the loop carrier 12. The wedge-shaped cutter 40 can be rounded off, as is shown here, or can alternatively taper to a point.

The loop 18 has an approximately semicircular shape. It can also be designed as an arc of an ellipse or an arc of a circle, with a greater or lesser extent than approximately 180°.

The loop 18 can have a cutting edge on the inside and/or outside or can be designed as a cutting blade. The cutting edge and the cutting blade can be directed inwards. Moreover, at least in the area of the connection element portion 20, the connection element 16 can also have a cutting edge on the inside and/or outside for resection of tissue or can be designed as a cutting blade. The cutting edge and the cutting blade can extend on the inside along the full length of the two strands 26, 30, in which case the cutting edge or cutting blade is oriented tangentially at each position of the strands.

The loop 18 and the connection element 16 can be formed from a stiff wire, in particular a steel wire. To improve the cutting action of the device 10 and to achieve simultaneous coagulation by the device 10, the loop 18 and the connection element 16 can be acted upon by high-frequency voltage and are designed to be electrically conductive. For this purpose, the connection element 16 has an electrical contact at the proximal end.

The loop carrier 12 can be rotated about its longitudinal axis 36 in a direction of rotation according to an arrow 42, such that the wedge-shaped cutter 40 points in the direction of rotation of the loop carrier 12. Upon rotation of the device 10, the wedge-shaped cutter 40 is in the lead and starts the cut, whereas the rest of the cut is effected by the remaining trailing portion of the loop 18. Moreover, tissue located to the sides of the connection element can be removed by the two strands 26, 30.

Figures 2A, 2B:
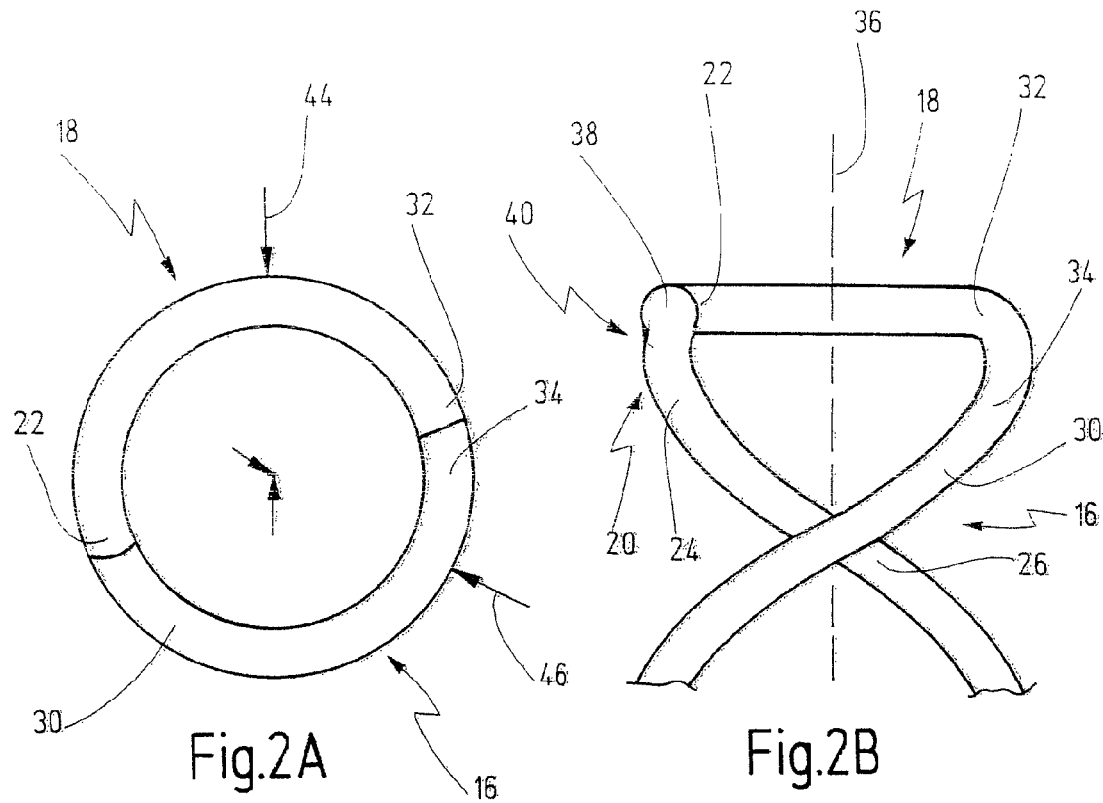
FIG. 2A shows a front view of the device from FIG. 1.
FIGS. 2B-2D show side views of the device from FIG. 1 in the area of its distal end.

FIG. 2A shows a plan view of the connection element 16 and the loop 18 from FIG. 1. The semicircular loop 18 lies in the plane of the drawing, since it extends in the plane approximately perpendicular to the longitudinal axis 36 of the loop carrier 12. The semicircular loop 18 has an outer radius 44 corresponding approximately to an outer radius 46 of the cylindrical connection element 16, i.e. of the two helical strands 26, 30. An outer radius of the loop carrier 12 can likewise be equal to or slightly smaller than the outer radius 44, 46, such that the device 10, in particular the connection element 16, can uniformly remove a tissue surface.

Figures 2C, 2D:
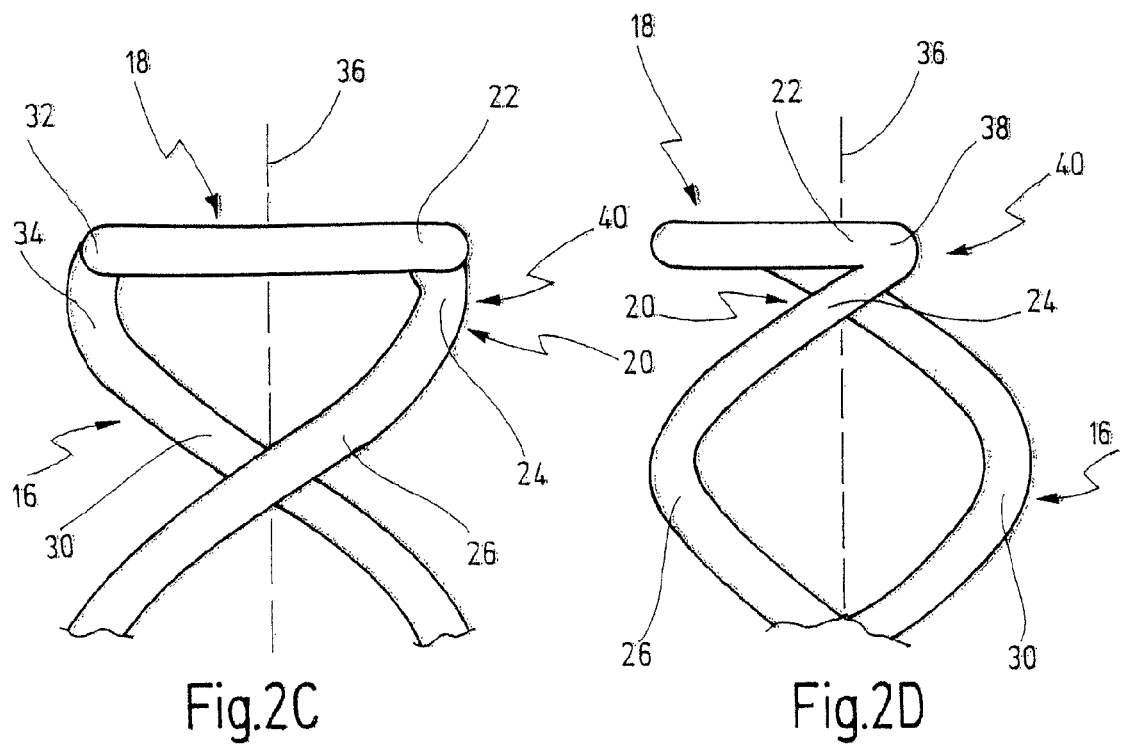

FIGS. 2B-2D show side views of the connection element 16 and of the loop 18 from FIG. 1, where FIG. 2B is a view of the inside of the loop, FIG. 2C is a view of the outside of the loop, and FIG. 2D is a view of the loop end portion 22 and the wedge-shaped cutter 40.

Figure 3A:
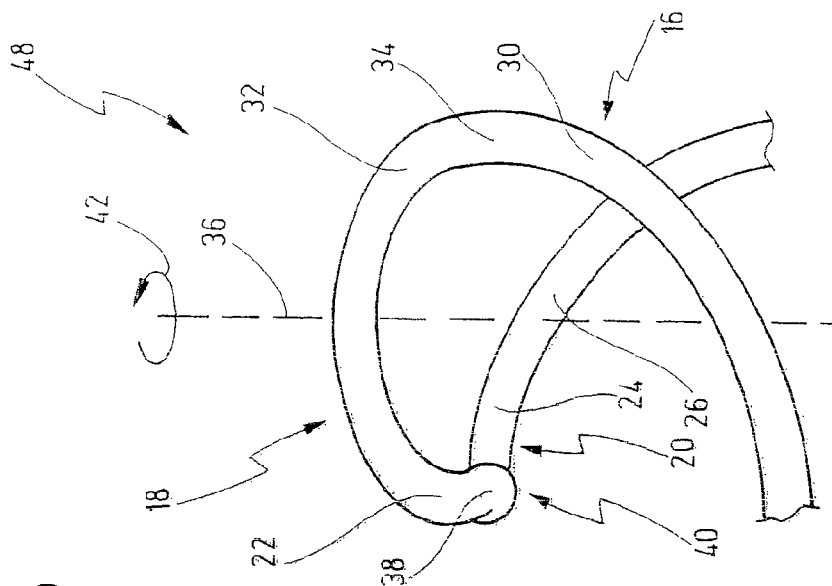
FIGS. 3A-3C show perspective views of the connection element and of the loop of the device from FIG. 1, in three rotation positions.
Figure 3B:
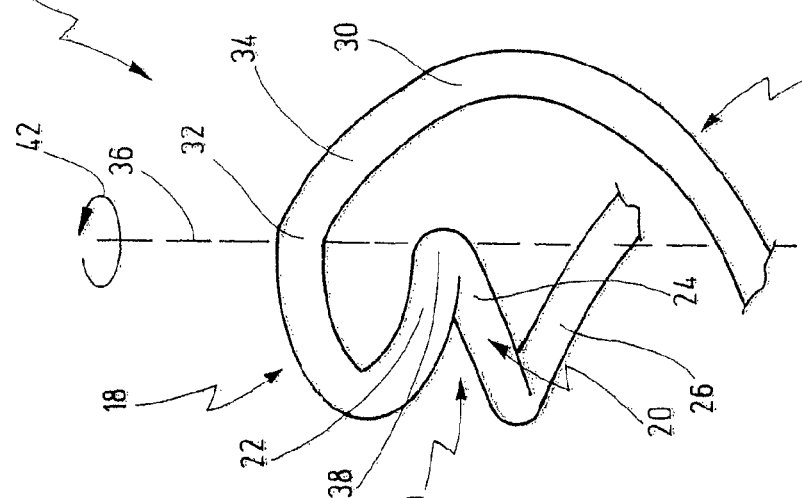
Figure 3C:
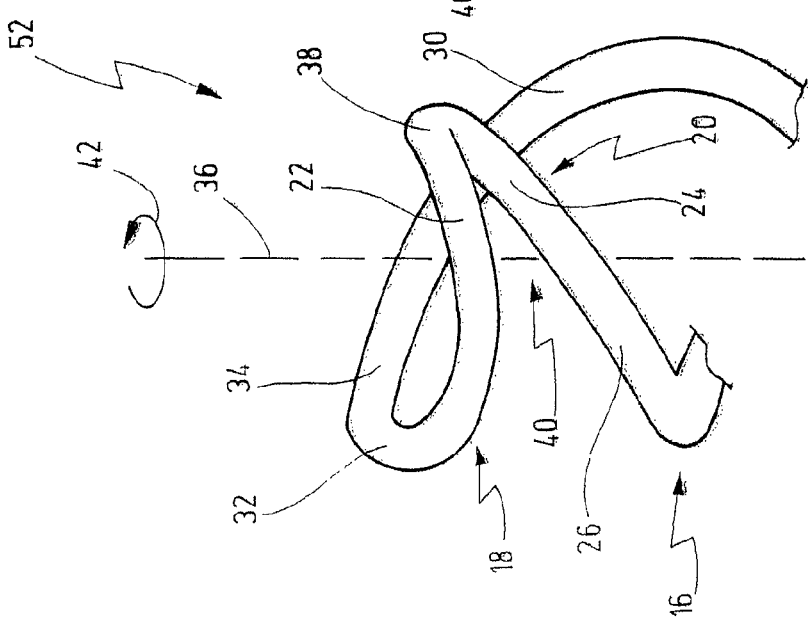

FIGS. 3A-3C show three rotation positions 48-52 of the connection element 16 and of the loop 18 from FIG. 1. In the first rotation position 48, the inside of the loop is shown in a perspective view and the wedge-shaped cutter 40 is directed out from the plane of the drawing. In the second rotation position 50, the loop 18 and the connection element 16 are rotated by approximately a further 90° about the longitudinal axis 36 of the loop carrier 12 in the direction of rotation indicated by the arrow 42. In a third rotation position 52, the loop 18 and the connection element 16 are rotated by approximately a further 60° in the direction of rotation indicated by the arrow 42.

Figure 4:
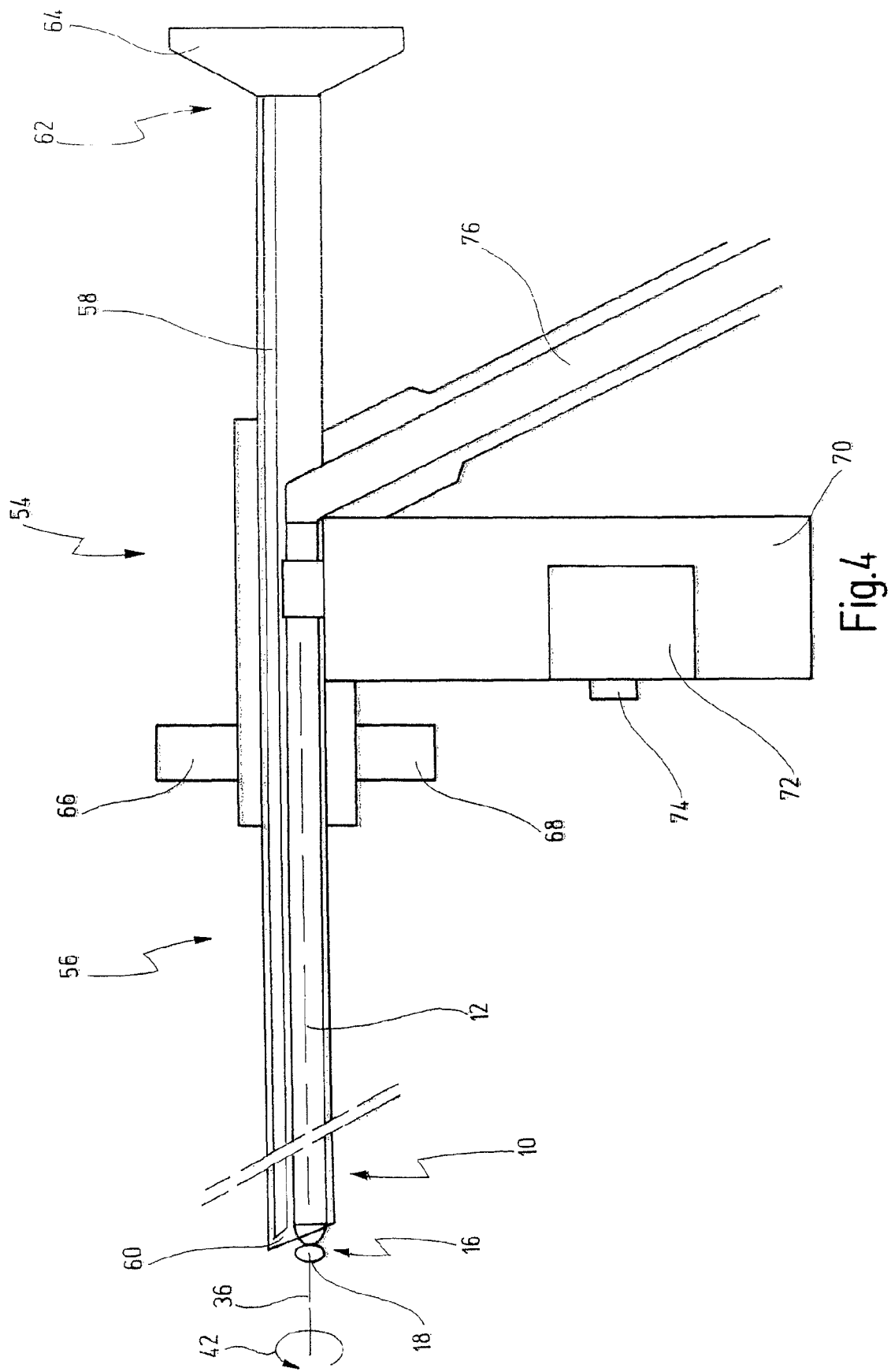
FIG. 4 shows a side view of a resectoscope in which the device from FIG. 1 is received.

FIG. 4 shows a resectoscope 54 in which the device 10 is received. The device 10 is arranged in a shaft 56 of the resectoscope 54, which is designed as a hollow tube. The shaft 56 moreover comprises an endoscope 58, which extends inside the shaft 56 from a distal end 60 of the resectoscope to an eyepiece 62 at a proximal end 64 of the resectoscope 54. Connector pieces 66, 68 for irrigation and suction lines are provided on the shaft 56 of the resectoscope 54. The connector pieces 66, 68 are used to deliver an irrigation liquid to the treatment site and to remove liquid from the treatment site. The resectoscope 54 moreover comprises a handle 70 in which a motor 72 for generating the rotation movement of the device 10 is received. The motor 72 can be actuated manually by means of a switch 74, here shown schematically as a push-button. The speed of rotation of the loop carrier 12, i.e. of the device 10, can be variably adjusted.

A suction line 76 to which a suction current can be applied is connected to the hollow tubular loop carrier 12, such that detached tissue can be suctioned off via the loop carrier 12 and the suction line 76.

The loop 18 and the connection element 16 protrude at least partially from the shaft 56 of the resectoscope 54. The helical strands 26, 30 each have a half winding, such that the loop 18 is only at a slight distance from the end of the shaft 56 of the resectoscope 54. Moreover, the loop 18 and the connection element 16 are always arranged within a viewing area of the endoscope 58.

What is claimed is:

1. A resectoscope for removing organic tissue by means of high-frequency current, comprising:
    a shaft for receiving a device that can be acted upon by high-frequency voltage, said device comprising:
        a loop carrier having a proximal end, a distal end, and a longitudinal axis extending from said proximal end to said distal end, said loop carrier able to rotate about said longitudinal axis relative to said shaft,
        a loop arranged at said distal end of said loop carrier and being able to be acted upon by high-frequency voltage, said loop having a loop end portion, said loop having an approximate semi-circular shape extending over approximately 180 degrees, said loop extending in a plane transverse to said longitudinal axis of said loop carrier, and
        a connection element connecting said loop with said loop carrier and having a distal connection element portion, said distal connection element portion extending obliquely with respect to the plane of the loop, said loop end portion and said distal connection element portion converging at an acute angle forming a wedge-shaped cutter having a point,
    wherein said wedge-shaped cutter points in a direction of rotation of said loop carrier.

2. The resectoscope of claim 1, wherein said connection element is designed in a helical line shape.

3. The resectoscope of claim 1, wherein said connection element has a first strand and a second strand, a distal end area of said first strand forming said wedge-shaped cutter together with said loop end portion, and a distal end area of said second strand being connected to an end of said loop opposite said loop end portion.

4. The resectoscope of claim 3, wherein said first strand and said second strand of said connection element are wound in the shape of helical lines running in opposite directions.

5. The resectoscope of claim 1, wherein said connection element has a cutting edge on an inside of said connection element at least in the area of said distal connection element portion.

* * * * *